(12) United States Patent
Singh

(10) Patent No.: US 7,687,041 B2
(45) Date of Patent: Mar. 30, 2010

(54) APPARATUS AND METHODS FOR UREA PRODUCTION

(75) Inventor: Vishnu D. Singh, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 190 days.

(21) Appl. No.: 12/038,285

(22) Filed: Feb. 27, 2008

(65) Prior Publication Data

US 2009/0216045 A1    Aug. 27, 2009

(51) Int. Cl.
   *B01J 19/00*         (2006.01)
   *C07C 273/02*    (2006.01)

(52) U.S. Cl. ........................... 422/191; 564/71; 564/72; 564/73; 422/193; 422/195; 422/198; 422/234; 202/158; 202/235; 261/158; 261/114.4; 261/114.5

(58) Field of Classification Search ........................ None
See application file for complete search history.

(56) References Cited

U.S. PATENT DOCUMENTS

| | | | |
|---|---|---|---|
| 3,258,486 A * | 6/1966 | Cook | ............................ 564/71 |
| 3,932,504 A | 1/1976 | Chen et al. | |
| 4,208,347 A | 6/1980 | Pagani | |
| 4,486,270 A | 12/1984 | Kaasenbrood | |
| 4,613,696 A * | 9/1986 | Zardi | ............................ 564/67 |
| 5,223,238 A | 6/1993 | Czuppon | |
| 5,523,483 A | 6/1996 | Singh et al. | |
| 5,580,236 A | 12/1996 | Pagani | |
| 5,736,116 A | 4/1998 | LeBlanc et al. | |
| 5,744,009 A | 4/1998 | Singh et al. | |
| 6,111,138 A | 8/2000 | Van Wijck et al. | |
| 6,254,840 B1 | 7/2001 | Mennen | |
| 6,392,096 B1 | 5/2002 | Mennen et al. | |
| 6,426,434 B1 | 7/2002 | Yoshida et al. | |
| 6,680,407 B2 | 1/2004 | Mennen | |
| 6,730,811 B1 | 5/2004 | Mennen | |
| 6,855,846 B2 | 2/2005 | Biermans et al. | |
| 6,875,892 B2 | 4/2005 | Filippi et al. | |
| 7,045,623 B2 | 5/2006 | Tjioe et al. | |

OTHER PUBLICATIONS

Bozzano, G. et al., New internals for urea production reactors, Journal of Chemical Technology and Biotechnology, 2003, pp. 128-133, 78, Society of Chemical Industry.

* cited by examiner

*Primary Examiner*—Jennifer A Leung
(74) *Attorney, Agent, or Firm*—Kellogg Brown & Root LLC

(57) ABSTRACT

Apparatus and methods for producing urea are provided. In one or more embodiments, an apparatus for producing urea can include a first zone, which can include a first flow channel in fluid communication with a first tube disposed about a first end of a plurality of trays, a second flow channel in fluid communication with a second tube disposed about the first end of the trays and a second end of the trays, and a third flow channel in fluid communication with a third tube disposed about the first and second ends of the trays. The apparatus can include a second zone, which can include a fixed bed comprising one or more inert packing materials disposed therein to provide additional surface area. The apparatus can include a third zone, which can include a plurality of tubes disposed therein. The second zone can be disposed between the first and third zones.

20 Claims, 2 Drawing Sheets

APPARATUS AND METHODS FOR UREA PRODUCTION

BACKGROUND

1. Field

The present embodiments generally relate to apparatus and methods for urea production.

2. Description of the Related Art

Urea can be synthesized by reacting ammonia and carbon dioxide to form ammonium carbamate, and subsequently dehydrated to form urea and water. The reaction of ammonia and carbon dioxide to form urea can be described using the following equilibrium reactions:

$2NH_3 + CO_2 \Leftrightarrow NH_2COONH_4$ (ammonium carbamate, exothermic)

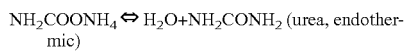

$NH_2COONH_4 \Leftrightarrow H_2O + NH_2CONH_2$ (urea, endothermic)

The first reaction producing ammonium carbamate is an exothermic reaction and essentially goes to completion. The second reaction for producing urea is endothermic and usually does not go to completion. The conversion of ammonium carbamate to urea increases as the temperature and $NH_3/CO_2$ ratio increase and decreases as the $H_2O/CO_2$ ratio increases. The resulting product can be a urea solution containing one or more contaminants, including ammonium carbamate, ammonia, carbon dioxide, and water, which must be removed to produce a purified urea product.

Conventional methods for removing contaminants in the urea solution have used multiple stages and multiple pieces of equipment. The equipment (i.e. high pressure carbamate condenser, high pressure ejector, medium pressure equipment, pumps, etc . . . ) is expensive to construct, install, maintain, and operate. The equipment must be fabricated out of material that can withstand high temperatures, pressures, and corrosive environments, which is expensive.

There is a need therefore, to reduce the amount of unconverted ammonium carbamate, ammonia, and water in the urea solution. Furthermore, there is a need to reduce the equipment cost required to produce urea.

BRIEF DESCRIPTION OF DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Apparatus and methods for producing urea are provided. In one or more embodiments, an apparatus for producing urea can include a first zone, which can include a first flow channel in fluid communication with a first tube disposed about a first end of a plurality of trays, a second flow channel in fluid communication with a second tube disposed about the first end of the trays and a second end of the trays, and a third flow channel in fluid communication with a third tube disposed about the first and second ends of the trays. The apparatus can include a second zone, which can include a fixed bed comprising one or more inert packing materials disposed therein to provide additional surface area. The apparatus can include a third zone, which can include a plurality of tubes disposed therein, the tubes defining a first flow path therethrough and a second flow path therearound, wherein the first and second flowpaths are not in fluid communication with one another but are situated to be in indirect heat exchange with one another. The second zone can be disposed between the first and third zones.

Figure 1:
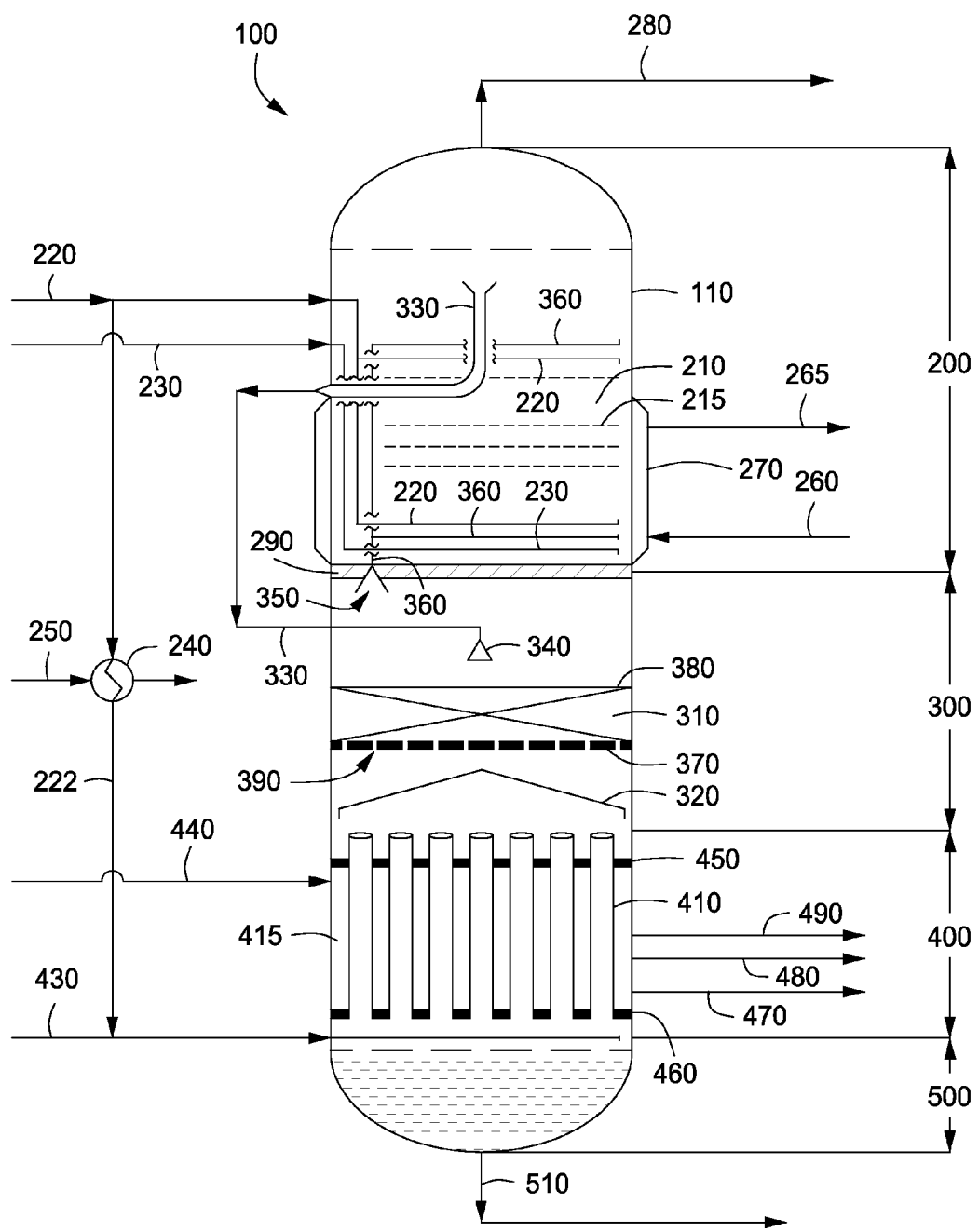
FIG. 1 depicts a partial cross sectional view of an illustrative reactor for producing urea, according to one or more embodiments described.

FIG. 1 depicts a partial cross sectional view of an illustrative reactor 100 for producing urea, according to one or more embodiments. In one or more embodiments, the reactor 100 can include a first zone 200, a second zone 300, and a third zone 400. The apparatus can include a fourth zone or collection zone 500. In one or more embodiments, the first zone 200 can include one or more reaction zones 210. A plurality of trays 215 can be at least partially disposed within the reaction zone 210. The first zone 200 can include one or more first tubes 230 disposed about a first end of the plurality of trays 215. The first zone 200 can include one or more second tubes 220 disposed about the first end and a second end of the plurality of trays 215. The first zone 200 can include one or more third tubes 360 disposed about the first end and the second end of the plurality of tubes 215.

In one or more embodiments, the second zone 300 can include at least one fixed bed 310. The fixed bed 310 can include, but is not limited to, one or more packed beds. The fixed beds 310 can include one or more packing materials to provide an increased surface area for contacting two or more fluids. The second zone 300 can include one or more baffles 320, one or more trays (not shown), and/or other structures (not shown) which can provide an increased surface area for contacting two or more fluids.

In one or more embodiments, the third zone 400 can include, but is not limited to, a plurality of tubes 410 disposed therein. The plurality of tubes 410 can define a first flow path through the third zone 400 and a second flow path around the tubes 410. The first flow path through the tube 410 sand the second flow path around the tubes 410 can be separate or independent (i.e. not in fluid communication) with one another, but can be situated to be in indirect heat exchange with one another.

In one or more embodiments, the second zone 300 can be disposed between the first zone 200 and the third zone 400. The third zone 400 can be disposed between the second zone 300 and the fourth zone 500. In one or more embodiments, the first zone 200, the second zone 300, and the third zone 400 can be devoid of a reactive catalysts. In one or more embodiments, one or more reactive catalysts can be disposed within the first zone 200, second zone 300, and/or third zone 400.

In one or more embodiments, one or more flow channels or conduits (one is shown 330) can be at least partially disposed within the first zone 200 at a first end thereof and at least partially disposed within the second zone 300 at a second end thereof. In one or more embodiments, at least a portion of the conduit 330 can be external to the reactor 100 at a position intermediate the first end and the second end. For example, the conduit 330 can exit the reactor 100 and re-enter a reactor wall 110 to provide fluid communication between the first zone 200 and the second zone 300. In one or more embodiments, the one or more conduits 330 can flow through (not shown) one or more section dividers 290 disposed between the first zone 200 and the second zone 300 to provide fluid communication between the first zone 200 and second zone 300. The conduit 330 can terminate at a first side 380 of the fixed bed 310. The conduit 330 can terminate adjacent a first side 380 of the fixed bed 310 with one or more distribution members or nozzles 340. Although not shown, the conduit 330 can include one or more valves or other flow rate control devices intermediate the first zone 200 and the second zone 300.

In one or more embodiments, the second zone 300 can be in fluid communication with the first zone 200 through one or more apertures or openings 350 disposed through the section divider 290. The one or more apertures 350 can be connected to the one or more third tubes 360 disposed within the first zone 200.

In one or more embodiments, at least two tubes or conduits 220 and 360, or as illustrated, three tubes or conduits 220, 230, and 360 can be in fluid communication with the reaction zone 210. In one or more embodiments, one or more tubes or conduits 430 can be in fluid communication with the plurality of tubes 410 disposed within the third zone 400. The tubes 430 can be in fluid communication with the third zone 400 opposite the side to which the second zone 300 is in fluid communication.

In one or more embodiments, the plurality of trays 215 at least partially disposed within the reaction zone 210 can be perforated trays, sieve trays, bubble, trays, floating valve trays, fixed valve trays, cartridge trays, dual flow trays, baffle trays, shower deck trays, disc and donut trays, orbit trays, horse shoe trays, snap-in valve trays, chimney trays, slit trays, or any combination thereof. The trays 215 can be made from or include process inert materials. For example, the trays 215 can include, but are not limited to, zirconium, titanium, duplex stainless steels, stainless steel alloys, non-ferrous metals, non-ferrous metal alloys, metal oxides, such as zirconium oxide, ceramic, glass, or any combination thereof. Any two adjacent trays 215 can be the same type of tray or different types of trays. The distance or spacing between any two adjacent trays can be the same or different.

In one or more embodiments, one or more heat exchangers 270 can be in heat exchange with the first zone 200. The heat exchanger 270 can be in indirect heat exchange with the reaction zone 210 disposed within the first zone 200. In one or more embodiments, the heat exchanger 270 can be, but is not limited to, a water jacket in indirect heat exchange with at least a portion of reactor wall 110. The water jacket can be disposed around at least a portion of the reactor wall 110 about the reaction zone 210. Although not shown, the heat exchanger 270 can be, but is not limited to, one or more tube coils, a plurality of U-tubes, straight tubes, or bayonet tubes (not shown) disposed within the reaction zone 210. In one or more embodiments, the tube coil, U-tubes, straight tubes, or bayonet tubes can include but are not limited to, one or more fins, static mixers, rifling, heat conductive packing, turbulence causing projections, or any combination thereof In one or more embodiments, the fixed bed 310 can include one or more materials that can increase the surface area within the fixed bed 310. In one or more embodiments, the one or more materials can include, but are not limited to, any material that is inert to the process. For example, the inert materials can include, ceramic, glass, zirconium, titanium, duplex stainless steels, stainless steel alloys, non-ferrous metals, non-ferrous metal alloys, metal oxides, such as zirconium oxide, or any combination thereof The particular inert material or materials can be chosen based upon the particular process composition, process conditions, the desired corrosion resistance, and economic factors, such as cost.

In one or more embodiments, the fixed bed 310 can be or include, but is not limited to, randomly packed material, structured packed material, one or more trays, one or more baffles, or any combination thereof The randomly packed material can include, but is not limited to, Nutter rings, I-rings, P-rings, R-rings, Raschig rings, saddle rings, A-PAK rings, Pall rings, U-rings, or any other known type of packing ring, or combination of packing rings. The structured packed material can include, but is not limited to, corrugated sheets, crimped sheets, gauzes, grids, wire mesh, monolith honeycomb structures, or any combination thereof. The one or more trays and/or baffles can include, but are not limited to, floating valve trays, fixed valve trays, sieve trays, bubble cap trays, cartridge trays, dual flow trays, baffle trays, shower deck trays, disc and donut trays, orbit trays, horse shoe trays, cartridge trays, snap-in valve trays, chimney trays, slit trays, plates, perforated trays, or any combination thereof.

In one or more embodiments, the fixed bed 310 can be supported by a bed support or screen 370 which can include one or more apertures or openings 390. The fixed bed 310 can be less than 1 m from the screen 370 to the top 380 of the fixed bed 310. The fixed bed 310 can be more than 1 m from the screen 370 to the top 380 of the fixed bed 310. The fixed bed 310 can range from about 0.25 m to about 5 m in height. In one or more embodiments, the thickness of the fixed bed 310 can range from about 0.25 m to about 1.25 m, or about 0.5 m to about 2 m, or about 0.5 m to about 3 m. The thickness of the fixed bed 310 can range from about 0.1 m, 0.2 m, 0.3 m, 0.4 m, or 0.5 m to about 0.6 m, or 0.7 m, or 0.8 m, or 0.9 m, or 1 m or 1.1 m.

Although not shown, in one or more embodiments, two or more fixed beds 310 can be disposed within the second zone 300. The two or more fixed beds 310 can be the same type of bed or different. For example, one packed bed can include randomly packed material and the second packed bed can include structured packed material. The two or more fixed beds 310 can be the same or different heights. For example one packed bed can be about 0.75 m and the second packed bed can be about 0.25 m in height.

In one or more embodiments, the openings 390 in the bed support 370 can be any shape or any combination of shapes. The openings 390 in the bed support 370 can be, but are not limited to, the shape of a circle, ellipse, square, rectangle, triangle, polygon, parallelogram, rhombus, trapezium, quadrilateral, crescent, oval, semi-circle, or any combination thereof. In one or more embodiments, the openings 390 can be smaller than the material disposed in the packed bed. The openings 390 can have a diameter ranging from a low of about 0.1 cm, or about 1 cm, or about 2 cm to a high of about 3 cm, or about 4 cm, or about 5 cm.

In one or more embodiments, a first tube sheet 450 and a second tube sheet 460 can be disposed about the plurality of tubes 410 disposed within the third zone 400, thereby forming an enclosed space or volume 415 about at least a portion of a length of the plurality of tubes 410. The plurality of tubes 410 can provide a flow path through the third section 400. The enclosed space 415 can provide a flow path around the third section 400. In one or more embodiments, one or more conduits 440 can be in fluid communication with the enclosed space 415. In one or more embodiments, conduit 470 can be in fluid communication with the enclosed space 415. In one or more embodiments, conduits 470, 480, and 490 (more or less conduits can be installed) can be in fluid communication with the enclosed volume 415 at different distances from the second tube sheet 460. Conduits 470, 480, and 490 can be independently closeable (not shown).

In one or more embodiments, the plurality of tubes 410 can extend above the first tube sheet 450. The plurality of tubes 410 can extend above the first tube sheet 450 by about 20 cm or more, or about 30 cm or more, or about 40 cm or more, or about 50 cm or more. The volume or space disposed above the first tube sheet 450 and the end of the plurality of tubes above the first tube sheet 450 can provide a pooling zone for liquids.

The plurality of tubes 410 can include an internal wall in the form of any shape. For example, the plurality of tubes 410 can have, but are not limited to, an internal wall in the shape of a circle, ellipse, square, rectangle, triangle, polygon, parallelogram, rhombus, trapezium, quadrilateral, crescent, oval, semi-circle, or any combination thereof. The length of the plurality of tubes 410 can be, but are not limited to, a length of from about 2 m to about 20 m. The length of the plurality of tubes can range from about 2 m, 5 m, or 8 m to about 10 m, 13 m, or 16 m. The plurality of tubes 410 can have a diameter that ranges from a low of about 1 cm, 2 cm, 3 cm, 4 cm, or 5 cm to a high of about 6 cm, 7 cm, 8 cm 9 cm, or 10 cm. In one or more embodiments, the plurality of tubes 410 can include but are not limited to, one or more fins, static mixers, rifling, heat conductive packing, turbulence causing projections, or any combination thereof.

In one or more embodiments, all or at least a portion of the components of the reactor 100 and conduits, e.g. 220, 230, 330, 430, 280, and 510, in fluid communication therewith, can be fabricated from, but are not limited to, zirconium, titanium, duplex stainless steels, steel, stainless steel, steel alloys, stainless steel alloys, non-ferrous metals, non-ferrous metal alloys, or combinations thereof. The particular material used to fabricate the reactor 100, components therein, or otherwise in fluid communication therewith can be based upon the process composition, process conditions, the desired corrosion resistance, and economic factors, such as cost.

In one or more embodiments, a first feed via line 230, a second feed via line 220, and a third feed via line 360 can be introduced to the first zone 200 via lines 220, 230, and 360, respectively. In one or more embodiments, the first feed via line 230 can include ammonium carbamate, the second feed via line 220 can include ammonia, and the third feed via line 360 can include ammonia and carbon dioxide. Although not shown, the first feed in line 230 and the second feed in line 220 can be combined and introduced to the reaction zone 210 via one tube or line, for example, line 220.

In one or more embodiments, the ammonium carbamate in the first feed via line 230 can contain about 25% wt to about 35% wt ammonia; about 35% wt to about 45% wt carbon dioxide; and about 25% wt to about 35% wt water. For example, the first feed can contain about 30.9% wt ammonia, about 40% wt carbon dioxide, and about 29.1% wt water. In one or more embodiments, the concentration of ammonia in the second feed introduced via line 220 to the reactor 100 can be about 95% wt, about 97% wt, about 99% wt, about 99.9% wt, about 99.99% wt, or more.

In one or more embodiments, the first feed, second feed, and third feed can be introduced to the first zone 200 at a pressure ranging from a low of about 150 kg/cm$^2$ (abs), 155 kg/cm$^2$ (abs), 158 kg/cm$^2$ (abs) to a high of about 162 kg/cm$^2$ (abs), 165 kg/cm$^2$ (abs), or 170 kg/cm$^2$ (abs). In one or more embodiments, the first feed, second feed, and third feed can be introduced to the first zone 200 at a pressure of from about 158 kg/cm$^2$ (abs) to about 162 kg/cm$^2$ (abs). The second feed can be introduced to the first zone 200 at a temperature ranging from about 10° C., 20° C., or 30° C. to about 50° C., 60° C., or 70° C. The second feed can be introduced to the first zone 200 at a temperature of from about 35° C. to about 45° C.

In one or more embodiments, the molar ratio of ammonia to carbon dioxide introduced to the reactor 100 can be from about 3.0 to about 4.0. The molar ratio of ammonia to carbon dioxide introduced to the reactor 100 can be from about 3.3 to about 3.7. The molar ratio of ammonia to carbon dioxide introduced to the reactor 100 can be about 3.5. In one or more embodiments, the water to carbon dioxide ratio within the reaction zone 210 can be from about 0.1 to about 1. The water to carbon dioxide ratio within the reaction zone 210 can be from about 0.4 to about 0.8. The water to carbon dioxide ratio within the reaction zone can be about 0.6.

In one or more embodiments, the ammonia, carbon dioxide, and ammonium carbamate can react in the reaction zone 210 to provide a first solution or solution. The first solution can include, but is not limited to, urea, ammonium carbamate, carbon dioxide, ammonia, and water. In one or more embodiments, the reaction zone 210 can be maintained at a reaction temperature ranging from about 170° C., 180° C., or 185° C. to about 191° C., 196° C., or 205° C. In one or more embodiments, the reaction zone 210 can be operated at a pressure ranging from about 150 kg/cm$^2$ (abs), 155 kg/cm$^2$ (abs), 158 kg/cm$^2$ (abs) to about 162 kg/cm$^2$ (abs), 165 kg/cm$^2$ (abs), or 170 kg/cm$^2$ (abs). In one or more embodiments, uncondensed gases can be present in the first zone 200. The uncondensed gases can be removed from an upper portion of the first zone 200 via line 280. The uncondensed gases can include, but are not limited to, ammonia, carbon dioxide, and inerts such as nitrogen and argon.

In one or more embodiments, a heat transfer medium can be introduced via line 260 to the heat exchanger 270. The heat transfer medium can remove at least a portion of the heat of reaction in the reaction zone 210 by indirect heat exchange. The heat transfer fluid via line 265 can be recovered from the heat exchanger 270. The heat transfer medium introduced via line 260 can be, for example, boiler feed water, which can be recovered via line 265 as steam.

In one or more embodiments, the conversion of ammonium carbamate to urea and water in the reaction zone 210 can be optimized by ensuring a sufficiently long residence time in the reactor. The plurality of trays 215 can ensure or otherwise control the residence time of the ammonium carbamate and the urea produced therefrom. The plurality of trays 215 can prevent or reduce back mixing of the ammonium carbamate and urea produced therefrom. In one or more embodiments, the residence time can be less than 2 hours, less than 1 hour, or less than 30 minutes. In one or more embodiments, the residence time can be 10 minutes or more, 20 minutes or more, or thirty minutes or more.

In one or more embodiments, the first solution or solution via line 330 can be dispersed or otherwise introduced to the fixed bed 310. The solution can be introduced to the conduit 330 in an upper portion of the first zone 200. The solution via line 330 can flow through the flow channel or conduit 330 to the second zone 300. In one or more embodiments, the first solution can be sprayed onto the fixed bed 310 with the one or more distribution members or nozzles 340. The solution can flow through the one or more fixed beds 310. The solution can flow through the fixed bed 310 counter-currently to a second gas mixture which can be introduced to the fixed bed 310 opposite the side the first solution is introduced. In one or more embodiments, the second gas mixture can include carbon dioxide, ammonia, and water. Although not shown, in one or more embodiments, one or more control valves can be used to control the flow rate of the solution through the conduit 330 to the second zone 300. The control valve can be manually or automatically controlled.

The conversion of ammonium carbamate to urea is an equilibrium reaction and the formation of urea can be adversely influenced by water present in the first section 200. In one or more embodiments, the solution, as it flows counter-currently to the second gas mixture can absorb at least a portion of the water present in the second gas mixture to provide a second solution and the third feed. The fixed bed 310 can provide an increase in surface area within the second zone 300, which can allow for greater contact between the first solution and the second gas mixture. The second solution exiting the fixed bed 310 can contain more water than the first solution. In one or more embodiments, the third feed can contain less water than the second gas mixture. In one or more embodiments, the third feed can be introduced to the reaction zone 210 by flowing through opening 350 which can be in fluid communication with the reaction zone 210 via the third flow channel or tube 360.

In one or more embodiments, the volume or space disposed between the first tube sheet 450 and the end of the plurality of tubes above the first tube sheet 450 can provide a pooling zone for the second solution. As the level of the second solution advances in the pooling zone to the end of the plurality of tubes above the first tube sheet 450, the solution can flow through the plurality of tubes 410.

In one or more embodiments, a gas mixture or first gas mixture via line 430 can be introduced to the third zone 400. The gas mixture can include, but is not limited to, ammonia and carbon dioxide. In one or more embodiments, the gas mixture can further include one or more oxidants. In one or more embodiments, the gas mixture in line 430 can contain from about 10% wt to about 20% wt ammonia, from about 80% wt to about 90% wt carbon dioxide, and from about 0% wt to about 5% wt oxidant. The one or more oxidants can include oxygen, air, oxygen enriched air or any other oxygen containing gas. The one or more oxidants can passivate or otherwise protect the materials used to construct the reactor 100, the internal components such as the plurality of trays 215, and the one or more conduits or tubes such as conduit 330.

In one or more embodiments, carbon dioxide in line 430 can be compressed by a compressor (not shown) to a pressure ranging from about 150 kg/cm$^2$ (abs) to about 170 kg/cm$^2$ (abs). Although not shown, in one or more embodiments, the one or more oxidants can be introduced to the compressor separately or with the carbon dioxide and compressed to provide compressed carbon dioxide and oxidant in line 430.

In one or more embodiments, the ammonia can be compressed using an ammonia compressor or pump (not shown) to a pressure ranging from about 150 kg/cm$^2$ (abs) to about 170 kg/cm$^2$ (abs). In one or more embodiments, the ammonia temperature prior to compression can be 10° C. or lower than its boiling point at its suction pressure. In one or more embodiments, at least a portion of the ammonia in line 220 can be introduced via line 222 to line 430. In one or more embodiments, the ammonia in line 222 can be pre-heated in a heat exchanger 240 by indirect heat exchange with a heat transfer fluid, such as steam introduced via line 250. The ammonia can be pre-heated to a temperature ranging from a low of about 120° C., about 140° C., or about 160° C. to a high of about 180° C., about 200° C., or about 220° C.

In one or more embodiments, at least a portion of the ammonia in line 220 can be introduced to the reaction zone 210. The ammonia via line 220 introduced to the reaction zone 210 can be from about 70 to about 90 percent of the total ammonia introduced into the reactor 100. In one or more embodiments, the ammonia introduced to the third zone 400 via line 430 can be from about 10 to about 30 percent of the total ammonia introduced into the reactor 100. In one or more embodiments, the ratio of the ammonia introduced via line 220 to the ammonia introduced via line 430 can be at a ratio of about 75:25, or about 80:20, or about 85:15.

In one or more embodiments, the gas mixture via line 430 can be introduced to the third zone 400 at a pressure ranging from about 150 kg/cm$^2$ (abs), 155 kg/cm$^2$ (abs), 158 kg/cm$^2$ (abs) to a high of about 162 kg/cm$^2$ (abs), 165 kg/cm$^2$ (abs), or 170 kg/cm$^2$ (abs). In one or more embodiments, the gas mixture via line 430 can be introduced to the third zone 400 at a pressure from about 158 kg/cm$^2$ (abs) to about 162 kg/cm$^2$ (abs). In one or more embodiments, the gas mixture via line 430 can be introduced at a temperature ranging from about 100° C. to about 200° C.

In one or more embodiments, the gas mixture can flow through the plurality of tubes 410, as discussed above, counter-currently to the second solution and toward the second zone 300. The first gas mixture can decompose at least a portion of the ammonium carbamate in the second solution to provide a urea solution and the second gas mixture. The urea solution can contain less ammonium carbamate and more water than the second solution. The second gas mixture can contain more ammonia, carbon dioxide, and water than the gas mixture introduced to the third zone via line 430. In one or more embodiments, the urea solution can be collected via line 510 from the collection zone 500.

In one or more embodiments, the urea solution in line 510 can contain urea, ammonium carbamate, water, ammonia, and carbon dioxide. The composition of urea in the urea solution can range from about 40 wt %, 45 wt %, or 50 wt % to about 55 wt %, 60 wt %, or 65 wt % urea. In one or more embodiments, the urea solution can contain from about 3% wt to about 15% wt ammonia, from about 5% wt to about 20% wt carbon dioxide, from about 20% wt to about 30% wt water, and from about 45% wt to about 65% urea. In one or more embodiments, the urea solution can contain from about 7.7% wt to about 11% wt ammonia, from about 9.9% wt to about 14% wt carbon dioxide, from about 24% wt to about 26% wt water, and from about 52% wt to about 56% wt urea.

In one or more embodiments, the plurality of tubes 410 in the third zone 400 can be indirectly heated by a heat transfer fluid via line 440. In one or more embodiments, the heat transfer fluid can be low pressure steam, medium pressure steam, high pressure steam, low temperature carbon dioxide shift effluent, medium temperature carbon dioxide shift effluent, or high temperature carbon dioxide shift effluent. In one or more embodiments, carbon dioxide shift effluent can be provided by a syngas production unit (not shown) by converting carbon monoxide to carbon dioxide. The heat transfer fluid via line 410 can flow through a second flow path around the plurality of tubes to indirectly heat the plurality of tubes 405 by introducing the heat transfer fluid to the enclosed space 415. The heat transfer fluid can be removed from the enclosed volume 415 via one or more lines 470, 480, or 490.

In one or more embodiments, the one or more lines 470, 480, and/or 490 can be chosen based upon the level or amount of condensate desired within the space 425. For example, as shown, line 490 can permit condensate to accumulate from the second tube sheet 460 to the level of line 490. As shown, line 470 can allow a less amount of condensate to collect around the plurality of tubes 410, with line 480 allowing an amount between that of line 490 and line 470. The desired level of condensate can be determined by the particular process conditions such as flow rates, temperatures, and pressures can be and adjusted accordingly via the particular line (i.e. 470, 480, 490). The heat transfer fluid introduced via line 440 can be at a pressure of from about 16 kg/cm$^2$ (abs) to about 24 kg/cm$^2$ (abs).

In one or more embodiments, water in the second gas mixture can be condensed out by the one or more baffles 320, the fixed bed 310, or other structures such as additional packed beds or trays (not shown) after the second gas mixture exits the third zone 400. The condensed water can add to or otherwise be absorbed by the solution and/or the second solution thereby providing the third feed.

Figure 2:
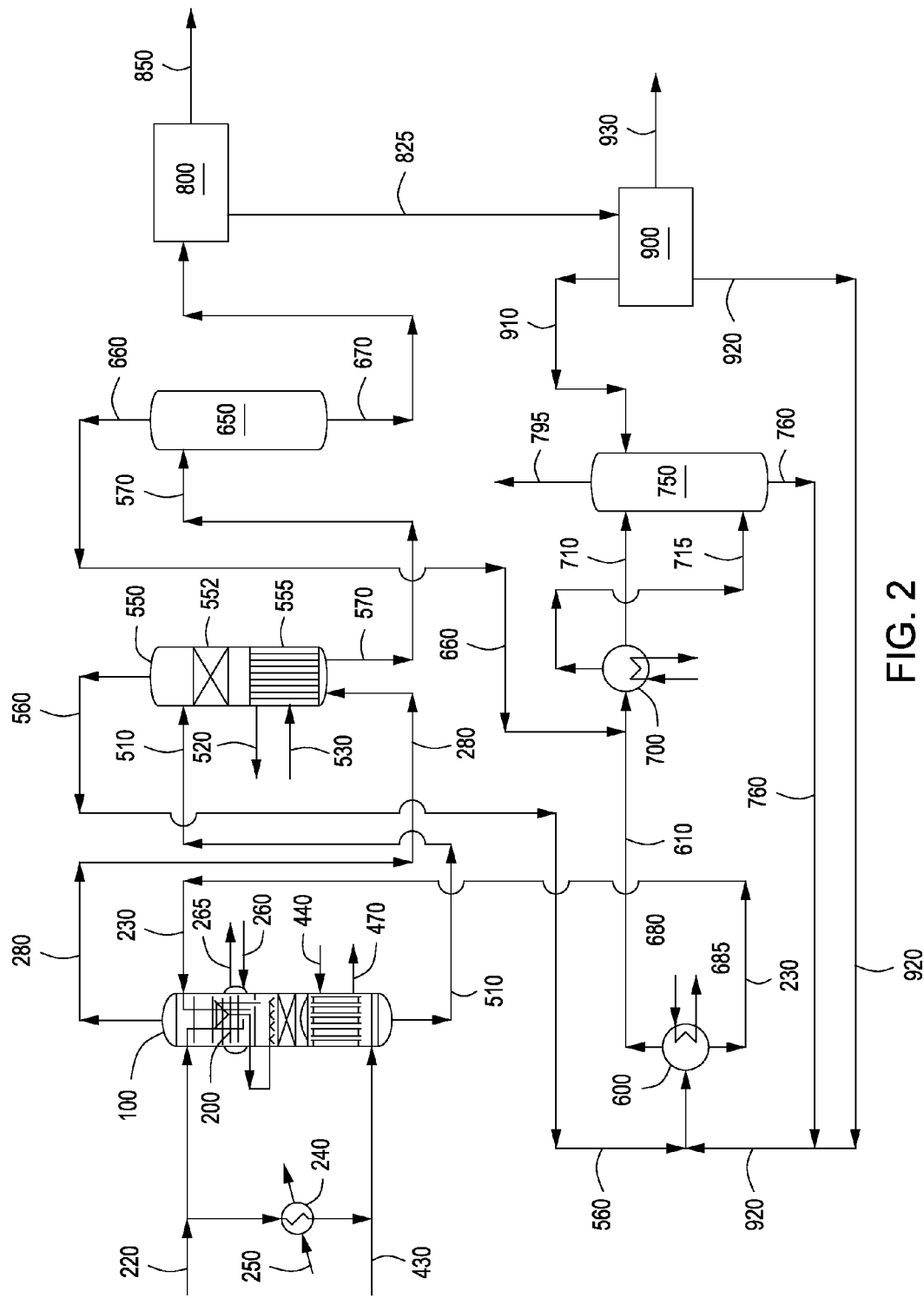
FIG. 2 depicts a schematic view of an illustrative system for producing urea, according to one or more embodiments described.

FIG. 2 depicts a schematic view of an illustrative system for producing urea, according to one or more embodiments. In one or more embodiments, the system for producing urea can include one or more reactors 100, low pressure decomposers 550, low pressure carbamate condensers 600, flash tanks 650, atmospheric condensers 700, atmospheric scrubbers 750, water removal systems 800, and clean up or purification systems 900.

In one or more embodiments, ammonia can be introduced via line 220 to reactor 100, as discussed above. The ammonia can be supplied by an ammonia unit or other sources (not shown). In one or more embodiments, carbon dioxide via line 430 can be supplied along with an optional oxidant (not shown) to the reactor 100. The carbon dioxide can also be supplied from an ammonia unit or other process (not shown). At least a portion of the ammonia in line 220 can be preheated by indirect heat exchange in heat exchanger 240 and introduced via line 222 (see FIG. 1) to the carbon dioxide and oxidant in line 430. Ammonium carbamate can be introduced to reactor 100 via line 230, which can be recycled ammonium carbamate from downstream processing steps, for example the low pressure carbamate condenser 600. The urea solution via line 510 and uncondensed gases via line 280 can be recovered from the reactor 100 as discussed and described above in reference to FIG. 1.

In one or more embodiments, the urea solution via line 510 can be introduced to the low pressure decomposer 550 to provide a first concentrated urea solution via line 570, which can contain less ammonium carbamate than the urea solution in line 510. The urea solution in line 570 can contain about 65% wt, about 69% wt, about 74% wt, or more urea. The urea solution in line 570 can contain less than about 5% wt, less than about 4% wt, less than about 3% wt, or less than about 2% wt ammonia. The urea solution in line 570 can contain less than about 4% wt, less than about 3% wt, less than about 2% wt, or less than about 1% wt carbon dioxide. The low pressure decomposer 550 can be operated at a pressure ranging from about 2 kg/cm$^2$ (abs), 4 kg/cm$^2$ (abs), or 5 kg/cm$^2$ (abs) to about 7 kg/cm$^2$ (abs), 8 kg/cm$^2$ (abs), or 10 kg/cm$^2$ (abs). The urea solution can be sprayed or otherwise dispersed onto a packed bed 552 disposed within the low pressure decomposer 550. The urea solution can flow through the packed bed 552 to one or more decomposer tubes 555 where at least a portion of the ammonium carbamate in the urea solution can be dissociated and evaporated to provide the first concentrated urea solution via line 570. Dissociating and evaporating at least a portion of the ammonium carbamate can cool the urea solution.

In one or more embodiments, the uncondensed gases from the first zone 200 can be introduced via line 280 to the decomposer tubes 555. The uncondensed gases can flow countercurrently to the urea solution through the decomposer tubes 555. The low pressure decomposer tubes 555 can be heated by indirect heat exchange with a heat transfer medium introduced via line 520 to a temperature of about 130° C. to about 150° C. The heat transfer medium can be recovered via line 530. The heat transfer medium can be low pressure or medium pressure steam. The decomposer tubes 555 can be of a shell-and-tube type arrangement. The uncondensed gases and heat from the heat transfer medium can decompose (dissociate and evaporate) at least a portion of the ammonium carbamate in the urea solution to provide evaporated ammonium carbamate gases and the first concentrated urea solution. The evaporated and dissociated ammonium carbamate gases, which can include ammonia, carbon dioxide and water and inerts from the uncondensed gases introduced via line 280 can be recovered via line 560 from the low pressure decomposer 550. The evaporated and dissociated ammonium carbamate gases via line 560 can be introduced to the low pressure carbamate condenser 600, which can provide at least a portion of the carbamate solution via line 230.

The evaporated and dissociated ammonium carbamate gases via line 560 can exit the low pressure decomposer 550 at a temperature of from about 50° C. to about 150° C.; or from about 60° C. to about 135° C.; or from about 65° C. to about 90° C. The evaporated and dissociated ammonium carbamate gases via line 560 can exit the low pressure decomposer 550 at a pressure ranging from about 2 kg/cm$^2$ (abs), or 4 kg/cm$^2$ (abs), or 5 kg/cm$^2$ (abs) to about 7 kg/cm$^2$ (abs), or 8 kg/cm$^2$ (abs), or 10 kg/cm$^2$ (abs). The low pressure carbamate condenser 600 can operate in a submerged manner and it can be cooled by cooling water introduced via line 680 and recovered via line 685. Uncondensed gases from the low pressure carbamate condenser 600 can be introduced to the atmospheric condenser 700 via line 610.

In one or more embodiments, the first concentrated urea solution in line 570 can have a urea concentration ranging from about 55 wt %, 60 wt %, 65 wt % to about 70 wt %, or 75 wt %, or 80 wt %. For example, the first concentrated urea solution in line 570 can have a urea concentration ranging from about 65 wt % to about 75 wt %. In one or more embodiments, the balance of the first concentrated urea solution can be water and minor amounts of ammonia and carbon dioxide. The water can range from about 15 wt %, 20 wt %, or 25 wt % to about 30 wt %, 35 wt % or 40 wt %. The ammonia and carbon dioxide can range from about 1 wt %, 2 wt %, or 3 wt % to about 4 wt %, or 5 wt %, or 6 wt %.

In one or more embodiments, the first concentrated urea solution in line 570 can be introduced to the one or more flash tanks 650, which can be operated at a pressure ranging from about 0.5 kg/cm$^2$ (abs), 0.8 kg/cm$^2$ (abs), or 1.0 kg/cm$^2$ (abs) to about 1.3 kg/cm$^2$ (abs), 1.5 kg/cm$^2$ (abs), or 1.7 kg/cm$^2$ (abs). For example, the one or more flash tanks 650 can be operated at a pressure of about 1.2 kg/cm$^2$ (abs). Although not shown, in one or more embodiments, one or more control valves can be used to control the flow rate of the first concentrated urea solution in line 570. The one or more control valves can be manual or automatic.

The first concentrated urea solution can be flashed adiabatically to a temperature of from about 100° C. to about 120° C. The flash tank 650 can remove ("flash") ammonium carbamate gases from the first concentrated urea solution which can include ammonia, carbon dioxide, and inerts such as nitrogen and/or oxygen to provide a second concentrated urea solution via line 670. In one or more embodiments, the flashed gases via line 660 can be removed from the flash tank 650. The flashed gases can be introduced to the uncondensed gases in line 610 which can then be introduced to the atmospheric condenser 700. The atmospheric condenser 700 can condense at least a portion of the ammonia and carbon dioxide in the gases to provide a weak carbamate solution via line 710 and uncondensed gases via line 715.

In one or more embodiments, the weak carbamate solution via line 710 can be sent to an upper section of the atmospheric scrubber 750 and uncondensed gases via line 710 can be sent to a lower section of the atmospheric scrubber 750. The atmospheric scrubber 750 can recover at least a portion of any residual ammonia and carbon dioxide gases by contacting the residual gases with the weak carbamate solution. The weak carbamate solution can be recovered via line 760 from the atmospheric scrubber 750 and uncondensed gases can be vented to the atmosphere via line 795.

The weak carbamate solution via line 760 can be introduced to the low pressure carbamate condenser 600 via line 920. At least a portion of any remaining gases in the weak carbamate solution can be sent through a cooler (not shown) and recycled back to the atmospheric scrubber 750 wherein ammonia and carbon dioxide can be scrubbed from the gases, condensed, added to the weak carbamate solution and recovered via line 760.

In one or more embodiments, the second concentrated urea solution via line 670 can contain from about 63% wt, 67% wt, or 70% wt to about 73% wt, 76% wt, or 80% wt urea. The remaining composition of the second concentrated urea solution can be water and minor amounts of ammonia and carbon dioxide. The water can range from about 20% wt, 23% wt, or 25% wt to about 27% wt, 30% wt or 35% wt. The ammonia and carbon dioxide can range from about 0.5% wt, 0.7% wt, or 1% wt to about 1.3% wt, 1.5% wt, or 2.0% wt.

In one or more embodiments, the second concentrated urea solution via line 670 can be introduced to the one or more water removal systems 800. In one or more embodiments, the water removal system 800 can include one or more storage tanks and vacuum evaporator/separator systems (not shown). The one or more storage tanks can temporarily store urea if required. In one or more embodiments, the second concentrated urea solution can be sent via either line 670 or from the one or more storage tanks to the one or more vacuum evaporator/separator units in the water removal system 800. In at least one specific embodiment, the second concentrated urea solution can be sent to two vacuum evaporator/separators (not shown) in the water removal system 800. The first vacuum evaporation/separator can be operated at a pressure ranging from about 0.1 kg/cm$^2$ (abs), 0.2 kg/cm$^2$ (abs), or 0.25 kg/cm$^2$ (abs) to about 0.35 kg/cm$^2$ (abs), 0.4 kg/cm$^2$ (abs) or 0.5 kg/cm$^2$ (abs). In one or more embodiments, the first vacuum evaporator/separator in the water removal system 800 can be operated at a temperature ranging from about 105° C., 115° C., or 125° C. to about 135° C., 140° C., or 145° C. In one or more embodiments, the second vacuum evaporator/separator in the water removal system 800 can be operated at a pressure ranging from about 0.01 kg/cm$^2$ (abs), 0.02 kg/cm$^2$ (abs), or 0.03 0.02 kg/cm$^2$ (abs) to about 0.04 kg/cm$^2$ (abs), 0.05 kg/cm$^2$ (abs) or 0.07 kg/cm$^2$ (abs). The second vacuum separator in the water removal system 800 can be operated at a temperature ranging from about 135° C. to about 145° C. In one or more embodiments, the second concentrated urea solution can be introduced to the one or more vacuum evaporation/separators in series, in parallel, or a combination thereof.

In one or more embodiments, a urea product ("urea melt") via line 850 can be provided from the water removal system 800. The urea melt can range from about 90 wt % to 99.99 wt % urea. The urea melt in line 850 can contain about 97% wt to about 99.99% wt urea and from about 0.01% wt to about 3% wt water. The concentration of the urea in the urea melt recovered via line 850 can depend on the number of vacuum separation steps employed and the desired urea melt purity. In one or more embodiments, the urea melt can be further processed to provide urea-formaldehyde resins, melamine, acylureas, urethanes, melamine-formaldehyde, urea prills and granules, derivatives thereof, and combinations thereof. In one or more embodiments, the urea melt in line 850 can be used as a fertilizer or in the synthesis of other fertilizers.

In one or more embodiments, a process condensate via line 825 can be provided from the water removal system 800, which can contain water, ammonia, carbon dioxide, and urea. The process condensate can contain from about 0.3 wt %, 0.5 wt %, or 0.7 wt % to about 0.9 wt %, 1.1 wt %, or 1.3 wt % urea. The process condensate can contain from about 3.5 wt %, 4.0 wt %, or 4.5 wt % to about 5.0 wt %, 5.5 wt %, or 6.0 wt % ammonia. The process condensate can contain from about 1.5 wt %, 1.8 wt %, or 2.0 wt % to about 2.2 wt %, 2.3 wt %, or 2.5 wt % carbon dioxide.

In one or more embodiments, the process condensate via line 825 can be sent to a cleanup system 900 to provide a purified process condensate, which can be sent off site for further purification or as boiler feed water for the complex or other uses (not shown) via line 930. An illustrative cleanup system 900 can include one or more second stage vacuum condensers, water tanks, and desorption and hydrolysis units (not shown) that can provide a weak carbamate solution via line 920 and one or more uncondensed gases via line 910. The weak carbamate solution can contain water, carbon dioxide, and ammonia. The uncondensed gases in line 910 can contain carbon dioxide, ammonia, and inerts, such as argon. The uncondensed gases can be introduced to the atmospheric scrubber 750 via line 910 for further scrubbing and/or venting to the atmosphere via line 795. The weak carbamate solution can be introduced to the low pressure carbamate condenser via line 920.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A apparatus for producing urea, comprising:
a first zone comprising a first flow channel in fluid communication with a first tube disposed about a first end of a plurality of trays, a second flow channel in fluid communication with a second tube disposed about the first end of the trays and a second end of the trays, and a third flow channel in fluid communication with a third tube disposed about the first and second ends of the trays;
a second zone comprising a fixed bed comprising one or more inert packing materials disposed therein to provide additional surface area; and
a third zone comprising a plurality of tubes disposed therein, the tubes defining a first flow path therethrough and a second flow path therearound, wherein the first and second flowpaths are not in fluid communication with one another but are situated to be in indirect heat exchange with one another, wherein the second zone is disposed between the first and third zones.

2. The apparatus of claim 1, further comprising a baffle disposed between the second and third zones, the baffle defining an annular flow path therearound.

3. The apparatus of claim 1, further comprising a tube sheet disposed in the third zone at a first end of the plurality of tubes, wherein a first end of the tubes extends beyond the tube sheet to provide a pooling zone for liquids.

4. The apparatus of claim 1, further comprising a heat exchanger in indirect heat exchange with the first zone.

5. The apparatus of claim 1, wherein the fixed bed comprises randomly packed material, structured packed material, or both.

6. The apparatus of claim 1, wherein the plurality of trays comprise sieve trays, floating valve trays, fixed valve trays, bubble trays, cartridge trays, dual flow trays, baffle trays, shower deck trays, disc and donut trays, orbit trays, horse shoe trays, cartridge trays, snap-in valve trays, chimney trays, slit trays, plates, perforated trays, or any combination thereof.

7. The apparatus of claim 1, wherein the fixed bed has a depth of from about 0.25 m to about 1.25 m.

8. An apparatus for producing urea, comprising:
a first zone comprising at least three flow channels at least partially disposed about a set of trays having a first end and second end, wherein:
a first flow channel is at least partially disposed about the first end of the trays,
a second flow channel is at least partially disposed about the first and second ends of the trays, and
a third flow channel is at least partially disposed about the first and second ends of the trays, wherein the flow channels are not in fluid communication with one another,
a second zone comprising a fixed bed comprising one or more inert packing materials disposed therein to provide additional surface area; and
a third zone comprising a plurality of tubes disposed therein, the tubes defining a first flow path therethrough and a second flow path therearound, wherein the first and second flowpaths are not in fluid communication with one another but are situated to be in indirect heat exchange with one another, wherein the second zone is disposed between the first and third zones, and wherein a fourth flow channel is at least partially disposed within the first zone at a first end thereof and at least partially disposed within the second zone at a second end thereof, and wherein at least a portion of the fourth flow channel is external to the first zone.

9. The apparatus of claim 8, wherein a distribution member is disposed at a second end of the fourth flow channel to distribute a fluid onto the fixed bed.

10. The apparatus of claim 8, further comprising a baffle disposed between the second and third zones, the baffle defining an annular flow path therearound.

11. The apparatus of claim 8, further comprising a tube sheet disposed in the third zone at a first end of the plurality of tubes, wherein a first end of the tubes extends beyond the tube sheet to provide a pooling zone for liquids.

12. The apparatus of claim 8, further comprising a heat exchanger in indirect heat exchange with the first zone.

13. The apparatus of claim 8, wherein the fixed bed comprises randomly packed material, structured packed material, or both.

14. The apparatus of claim 8, wherein the plurality of trays comprise sieve trays, floating valve trays, fixed valve trays, bubble trays, cartridge trays, dual flow trays, baffle trays, shower deck trays, disc and donut trays, orbit trays, horse shoe trays, cartridge trays, snap-in valve trays, chimney trays, slit trays, plates, perforated trays, or any combination thereof.

15. The apparatus of claim 8, wherein the fixed bed has a depth of from about 0.25 in to about 1.25 m.

16. The apparatus of claim 8, wherein the first zone, second zone and third zone are devoid of a reactive catalyst.

17. A method for producing urea, comprising:
introducing ammonia, ammonium carbamate, and carbon dioxide to an apparatus for producing urea, the apparatus comprising:
a first zone comprising a first flow channel in fluid communication with a first tube disposed about a first end of a plurality of trays, a second flow channel in fluid communication with a second tube disposed about the first end of the trays and a second end of the trays, and a third flow channel in fluid communication with a third tube disposed about the first and second ends of the trays;
a second zone comprising a fixed bed comprising one or more inert packing materials disposed therein to provide additional surface area; and
a third zone comprising a plurality of tubes disposed therein, the tubes defining a first flow path therethrough and a second flow path therearound, wherein the first and second flowpaths are not in fluid communication with one another but are situated to be in indirect heat exchange with one another, wherein the second zone is disposed between the first and third zones,
contacting the ammonia, ammonium carbamate, and carbon dioxide within the first zone at conditions sufficient to provide a solution comprising urea, ammonium carbamate, carbon dioxide, ammonia, and water;
flowing the solution to the second zone, wherein the solution is distributed about the fixed bed; and
flowing the distributed solution through the third zone, wherein the solution flows through the tubes countercurrently to a gas mixture comprising ammonia and carbon dioxide, thereby providing a second gas mixture and a second solution comprising urea, ammonia, ammonium carbamate, and water; wherein the second gas mixture flows counter-currently through the second zone, contacting the distributed solution and continues flowing to the first zone contacting the ammonia and ammonium carbamate therein.

18. The method of claim 17, wherein the first zone operates at a pressure of from about 150 kg/cm2 (abs) to about 170 kg/cm2 (abs) and a temperature of from about 175° C. to about 200° C.

19. The method of claim 17, wherein the ammonia is introduced to the first zone and the third zone, wherein the ratio of ammonia introduced to the first zone to the third zone is from about 75:25 to about 85:15.

20. The method of claim 17, wherein the ammonia and carbon dioxide are supplied the apparatus at a ratio of from about 3.3 to about 3.5.

* * * * *